United States Patent [19]

Lafon

[11] Patent Number: 5,180,745

[45] Date of Patent: Jan. 19, 1993

[54] METHOD FOR PROVIDING A NEUROPROTECTIVE EFFECT

[75] Inventor: Louis Lafon, Paris, France

[73] Assignee: Laboratoire L. Lafon, Maisons Alfort Cedex, France

[21] Appl. No.: 713,376

[22] Filed: Jun. 13, 1991

[30] Foreign Application Priority Data

Jun. 14, 1990 [FR] France ................. 90 07442

[51] Int. Cl.⁵ .......................................... A61K 31/165
[52] U.S. Cl. ................................................... 514/618
[58] Field of Search ........................................ 514/618

[56] References Cited

U.S. PATENT DOCUMENTS 4,066,686  1/1978  Lafon ................................. 562/621
4,177,290  12/1979  Lafon ................................. 424/324
4,927,855  5/1990  Lafon ................................. 514/618

OTHER PUBLICATIONS

CA93(1):7872q, Lafon, 1979.
CA109(15):122357m, Goldenberg, 1988.
CA 107(13):109236k, Milhand, 1987.

Primary Examiner—Leonard Schenkman
Assistant Examiner—Kimberly R. Jordan
Attorney, Agent, or Firm—Wegner, Cantor, Mueller & Player

[57] ABSTRACT

The present invention relates to a method for providing a patient with neuroprotective effect, which consists in administering modafinil to said patient.

1 Claim, No Drawings

METHOD FOR PROVIDING A NEUROPROTECTIVE EFFECT

The present invention relates to a novel use of modafinil.

Modafinil or benzhydrylsulfonyl acetamide is a compound of formula:

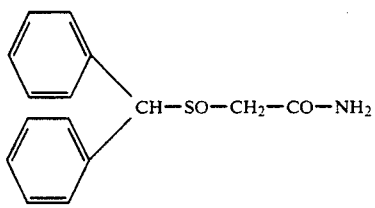

This compound and its therapeutic use as a stimulant of the central nervous system have been described in FR-A-2 385 693.

It has now been discovered that modafinil possesses a neuroprotective effect which may be used in therapy, in particular in the treatment of Parkinson's disease and other degenerative diseases of the central nervous system.

Consequently, the object of the present invention is the use of modafinil for providing a neuroprotective effect in a human patient.

The neuroprotective medicine containing modafinil is available, in particular, in a form suitable for oral administration. The doses administered to human subjects usually vary from 50 to 1000 mg.

Hereafter, the results of pharmacological tests will be given which demonstrate the neuroprotective effects of modafinil.

Mice to which MPTP (1-methyl-4-phenyl-1,2,3,6-tetrahydropyridine) has been administered were used in some of these tests. MPTP triggers parkinsonian symptoms in the mouse by the destruction of the nigrostriatal nerve fibers, which is followed by a depletion of dopamine. MPTP leads to the production of a model of Parkinson's disease which is considered to be reliable.

1. Effect of Modafinil on the Disappearance of $^3$H-mazindole Binding from the Neostriatal Membranes Induced by MPTP in the Adult Black Mouse The method described by Javitch et al. is used (Mol. Pharmacol., 26, p. 35, 1984).

MPTP (1-methyl-4-phenyl-1,2,3,6-tetrahydropyridine) is injected subcutaneously into adult male mice of the C57 bl/6 strain at a dose of 40 mg/kg. 15 Minutes later modafinil is injected in a 0.4% suspension of carboxymethylcellulose sodium by the intraperitoneal route and the injection is repeated once a day for 14 days.

$^3$H-mazindole (15 Ci/mmol), a radioligand which binds dopamine, is used at a concentration of 60 nM.10 uM mazindole was used to determine specific binding.

Table I presents the results obtained.

| Modafinil dose mg/kg | Binding of $^3$H-mazindole (neostriatum) dpm/mg prot* |
|---|---|
| 0 | 28810 ± 215 |
| 10 | 36820 ± 216 |
| 30 | 40130 ± 126 |
| 100 | 66460 ± 206 |

*dpm/mg prot: disintegrations per minute/mg of protein.

These results demonstrate a dose-dependent protective effect of modafinil.

2. Effect of Modafinil on the Degeneration of Striatal DA Nerve Terminals Induced by MPTP in the Black Mouse The method described by Agnati et al. (Neuroscience 26, 461, 1988) is used.

MPTP is injected at a dose of 40 mg/kg by the intraperitoneal route. 15 minutes later modafinil is injected by the intraperitoneal route in a 0.4% suspension of carboxymethylcellulose sodium and the injection is repeated each day. The animals are sacrificed 14 days after the injection of MPTP. The immunoreactivity (IR) of the tyrosine hydroxylase is measured by image analysis in samples of median neostriatum.

Table II presents the results obtained.

| Modafinil dose mg/kg | Immunoreactivity value |
|---|---|
| 0 | 151 ± 17.8 |
| 10 | 364 ± 63.9 |
| 30 | 426 ± 99.2 |
| 100 | 520 ± 121 |

These results demonstrate that modafinil exerts a protective effect against the neurotoxicity of MPTP in a dose-dependent manner.

The amount of dopamine stored in the neurones of the substantia nigra was also measured using the same experimental model.

Table III presents the results obtained:

| Treatment | Dopamine mg/g tissue |
|---|---|
| MPTP | 144 ± 16 |
| MPTP + modafinil 10 mg/kg | 309 ± 45 |
| MPTP + modafinil 100 mg/kg | 325 ± 26 |

Modafinil counteracts the depletion of the dopamine level induced by MPTP in a dose-dependent manner.

3. Effect of Modafinil on the Degeneration of the Nigrostriatal DA Neurones Subsequent to Partial Hemitransection in the Male Rat The treatment with modafinil is begun 15 minutes after partial hemitransection (according to the method of Agnati et al., Acta Physiol. Scand. 119, 347) at a dose of 30 mg/kg for a period of 15 consecutive days. This surgical lesion leads to a diminution of the amount of dopamine stored in the subcortical limbic area (nucleus accumbens and tuberculum olfactorium) with partial neurodegeneration of the dopaminergic nerve terminals, total depletion of the dopamine stored in the neostriatum and to modifications in the serotonin content of the substantia nigra. A pharmacological activity of modafinil has been observed on the area not affected by the surgical lesion and on areas both affected and unaffected by the lesion in the subcortical limbic region.

I claim:

1. A method for the treatment of Parkinson's disease which comprises administering to a patient in need thereof a therapeutically effective amount of modafinil.

* * * * *